[19] United States Patent
Foster et al.

[11] Patent Number: 5,021,257
[45] Date of Patent: Jun. 4, 1991

[54] HOT-MELT ADHESIVE COMPOSITION

[75] Inventors: Bruce W. Foster; Clyde N. Clubb; Richard K. Stuart, Jr., all of Longview, Tex.

[73] Assignee: Eastman Kodak Company, Rochester, N.Y.

[21] Appl. No.: 415,816

[22] Filed: Oct. 2, 1989

Related U.S. Application Data

[60] Division of Ser. No. 314,626, Feb. 23, 1989, Pat. No. 4,886,853, which is a continuation-in-part of Ser. No. 126,439, Nov. 30, 1987, abandoned.

[51] Int. Cl.$^5$ .................. A61K 47/32; C08K 5/01; C09J 3/14
[52] U.S. Cl. .................. 427/2; 524/477; 524/478; 524/480; 524/487; 524/488; 524/489; 524/476
[58] Field of Search .................. 427/208.2, 2

[56] References Cited

U.S. PATENT DOCUMENTS

| | | | |
|---|---|---|---|
| 3,278,504 | 10/1966 | Eells et al. | 282/8 A |
| 3,341,621 | 9/1967 | Hagemeyer, Jr. et al. | 525/323 |
| 3,376,250 | 4/1968 | Newland et al. | 524/175 |
| 3,409,585 | 11/1968 | Hagemeyer, Jr. et al. | 524/579 |
| 3,519,586 | 7/1970 | Guillet et al. | 524/579 |
| 3,642,678 | 2/1972 | Shepard et al. | 524/487 |
| 3,872,064 | 3/1975 | Pace et al. | 526/339 |
| 3,923,758 | 12/1975 | Carter, Jr. et al. | 526/152 |
| 3,954,697 | 5/1976 | McConnell et al. | 526/348.3 |
| 4,022,728 | 5/1977 | Trotter et al. | 524/274 |
| 4,049,752 | 9/1977 | Albers | 525/263 |
| 4,072,735 | 2/1978 | Ardemagni | 524/274 |
| 4,072,812 | 2/1978 | McConnell et al. | 526/348.2 |
| 4,072,813 | 2/1978 | McConnell et al. | 526/348.2 |
| 4,105,718 | 8/1978 | Weemes et al. | 525/232 |
| 4,112,208 | 9/1978 | McConnell et al. | 525/387 |
| 4,120,916 | 10/1978 | Meyer, Jr. et al. | 525/240 |
| 4,146,521 | 3/1979 | Godfrey | 524/274 |
| 4,146,586 | 3/1979 | McConnell et al. | 525/174 |
| 4,178,272 | 12/1979 | Meyer, Jr. et al. | 525/210 |
| 4,210,570 | 7/1980 | Trotter et al. | 524/271 |
| 4,217,428 | 8/1980 | McConnell et al. | 525/210 |
| 4,259,470 | 3/1981 | Trotter et al. | 526/348.2 |
| 4,264,756 | 4/1981 | Trotter et al. | 526/348.2 |
| 4,288,358 | 9/1981 | Trotter et al. | 524/474 |
| 4,299,745 | 11/1981 | Godfrey | 524/488 |
| 4,471,086 | 9/1984 | Foster | 524/489 |
| 4,526,577 | 7/1985 | Schmidt, Jr. et al. | 604/366 |
| 4,567,223 | 1/1986 | Ames | 525/210 |
| 4,719,260 | 1/1988 | Stuart, Jr. et al. | 525/285 |
| 4,749,739 | 6/1988 | Foster et al. | 524/271 |
| 4,761,450 | 8/1988 | Lakshmanan et al. | 524/487 |
| 4,833,192 | 5/1989 | Lakshmanan et al. | 524/487 |

FOREIGN PATENT DOCUMENTS 51768 3/1985 Japan .
1302283 1/1973 United Kingdom .

*Primary Examiner*—Melvyn I. Marquis
*Assistant Examiner*—David Rowley
*Attorney, Agent, or Firm*—Thomas R. Savitsky; William P. Heath, Jr.

[57] ABSTRACT

The present invention is directed to a hot-melt adhesive containing at least one propylene/1-hexane copolymer. The adhesive contains an amount of a low viscosity, substantially crystalline wax, having a melting point of about 90° C. to about 125° C., sufficient to improve the elastic delamination resistance of the adhesive. The adhesive are particularly useful in disposable diaper construction.

6 Claims, No Drawings

HOT-MELT ADHESIVE COMPOSITION

This is a divisional of copending application Ser. No. 07/314,626 filed on Feb. 23, 1989, now Pat. No. 4,886,853 which is a continuation-in-part of Ser. No. 126,439, filed on Nov. 30, 1987, which has been abandoned.

FIELD OF INVENTION

The present invention concerns hot-melt adhesives (HMAs) containing at least one propylene/hexene copolymer useful as disposable diaper adhesives.

BACKGROUND OF THE INVENTION

Recent trends in the design of disposable diapers have necessitated the development of more versatile adhesives for use in the diapers. The trend of the industry toward diapers with elastic bands on either the legs or the waist of the diaper have made it necessary to use a stronger more delamination resistant adhesive to hold the elastic in place. Most diaper manufacturers prefer to use one hot-melt adhesive to both construct the diaper (that is to bind the nonwoven top sheet and filler to the polyethylene back sheet) and to hold the elastic on the leg or waist of the diaper. It is well known that polyolefin based HMAs are suitable for the construction of diapers by construction techniques as currently practiced such as multiple fine line, hot-melt spray, hot-melt foam, slot coating operations, and various screen coating methods. However, polyolefin-based HMAs are traditionally not suitable for the bonding of the elastic to the diapers, that is, the elastic delamination resistance is insufficient for such an application. For this reason, adhesives based on styrene rubbers such as S-I-S block copolymers or S-B-S block copolymers are used (see, for example, U.S. Pat. No. 4,526,577).

The use of two HMAs on the same diaper poses some problems for the diaper manufacturer. They must insure the right adhesive is used in the right melt tank and is applied to the correct place on the diaper. Therefore, an adhesive that is capable of performing both types of bonding functions is highly desirable.

Wax is traditionally added to hot-melt adhesives with the objective of controlling viscosity of the adhesive. That is, it is a diluent and may in some cases lower the cost of the adhesive. For the most part waxes are not known to add to the strength of HMAs but rather are used to control set time or open time or viscosity.

This invention describes a polyolefin-based HMA suitable for use as both the adhesive of construction of disposable diapers and as the adhesive to hold the elastic onto the leg or waistband. Thus a universal diaper adhesive based on polyolefins has been developed. It has been surprisingly found that the addition of a low viscosity, substantially crystalline wax to a polyolefin-based HMA substantially improves the elastic delamination resistance. The formulation of an HMA containing an olefin-based polymer having sufficient elastic delamination resistance to meet the demands of the universal diaper adhesive is a significant advance in the art.

SUMMARY OF THE INVENTION

The present invention is directed to a hot-melt adhesive composition which has a blend of properties that makes it ideally suited for use with disposable diapers.

More specifically, the present invention is directed to a hot-melt adhesive composition having a viscosity of about 3,000 to about 25,000 centipoise at 135° C. and a Ring and Ball softening point of about 90° C. to about 125° C., said adhesive compostion comprising a blend of:

(a) at least one substantially amorphous propylene/hexene copolymer having an acid number of less than about 0.5, (b) at least one tackifier, and (c) at least one substantially crystalline, low viscosity hydrocarbon wax containing substantially no propylene and having a melt viscosity of from about 3 to about 4,000 centipoise at 150° C. and a melting point of from about 90° C. to about 125° C., the concentration of components (a), (b), and (c) being such that said adhesive composition has an elastic delamination resistance of at least about 4 hours wherein elastic delamination resistance is the length of time a polyethylene to elastic bond can withstand the stress of elastic relaxation at body temperature.

Most preferably, the composition of the present invention is a hot-melt adhesive composition having a viscosity of about 3,000 to about 25,000 centipoise at 135° C. and a Ring and Ball softening point of about 90° C. to about 125° C., said composition comprising a blend of:

(i) about 30 to about 70 weight percent of at least one substantially amorphous propylene/hexene random copolymer containing from about 20 to about 50 weight percent of 1-hexene, said polymer having a melt viscosity of from about 2,000 to about 20,000 centipoise at 190° C., (ii) about 20 to about 50 weight percent of at least one solid tackifier comprising hydrocarbon resins or polyterpene resins, said solid tackifier having a Ring and Ball softening point of from about 70° C. to about 145° C., (iii) 0 to about 30 weight percent of at least one liquid tackifier having a viscosity of from about 5 to about 500 centipoise at 95° C. and a Ring and Ball softening point of from about 5° C. to about 30 ° C., (iv) from about 1 to about 10 weight percent of at least one substantially crystalline, low viscosity hydrocarbon wax containing substantially no propylene and having a melt viscosity of from about 3 to about 4,000 centipoise at 150° C. and a melting point of from about 90° C. to about 125° C., and (v) 0 to about 30 weight percent of at least one plasticizing oil.

The present invention is also directed to a method for applying the compositions of the invention to a disposable diaper and to articles comprising the composition of the invention in combination with a disposable diaper.

DETAILED DESCRIPTION OF THE INVENTION

The adhesive compositions of the present invention preferably have a melt viscosity of about 4,000 to about 10,000 centipoise at 135° C., more preferably about 5,000 to about 9,000. Melt viscosities of the adhesive compositions and the various components thereof can be determined using a Brookfield Model RTV Thermosel viscometer using a Number 27 spindle in accordance with American Society for Testing and Materials (ASTM) Procedure 1824-66.

The adhesive compositions of the present invention preferably have a Ring and Ball softening point (RBSP) of about 100° C. to about 125° C., more preferably about 112° C. to about 120° C. RBSP for the adhesive compositions and various components thereof can be determined by use of ASTM Procedure E-28.

The Gardner color of the adhesive compositions of the present invention preferably is less than about 7, most preferably less than about 3. Gardner color for the adhesive compositions and various components thereof can be determined by use of ASTM Procedure D-1544.

Bond strength of the adhesives of the present invention is at least about 200 grams based on an adhesive coating weight of 2.1 milligrams (mg) per inch, preferably at least 300 grams. At about 300 grams substrate failure occurs. Bond strength can be measured by the controlled destruction of the bonds by an Instron tensile tester at 10 inches per minute (min.). More specifically, nonwoven fabric (e.g., polypropylene or polyester nonwoven fabric commonly used in disposable diaper construction) is bonded by applying a single 2.1 mg per inch bead of adhesive on a moving web of polyethylene film at a melt temperature of 140° C., then applying sufficient nip pressure to bring the two substances in contact. The open time is about 1 second, and the compression time is less than 0.5 seconds. The nonwoven fabric is then pulled from the polyethylene in a T-peel mode and the average amount of force required to pull apart the two substances is the bond strength.

Tensile strength of the adhesive compositions of the present invention is typically greater than about 10 pounds per square inch (psi), and preferably about 20 to about 50 psi. Tensile strength can be determined by use of ASTM Procedure D-638-72.

The Cone penetration value of the adhesive compositions of the present invention is typically greater than about 10 decimillimeters (dmm), and preferably greater than about 20 dmm. Cone penetration can be measured by use of ASTM Procedure D-1403.

The elastic delamination resistance of the compositions of the present invention is greater than about 4 hours, preferably greater than about 8 hours, more preferably greater than about 24 hours, and most preferably greater than about 100 hours. The elastic delamination resistance is determined by the following procedure:

Elastic, 0.25 inches wide and 0.007 inches thick, typically used in disposable diaper contruction (can be obtained from Fulflex Company) is expanded to 100% elongation. Test adhesive is applied as a bead at 275° F. to the elongated elastic which is then immediately brought into contact with polyethylene film and passed through a compression roller. The hot-melt adhesive bead weight is controlled at 10 to 15 mg per linear inch of polyethylene film. The polyethylene film is 1–2 mils thick and is a low density polyethylene blended with linear low density polyethylene or high density polyethylene. The polyethylene film is pigmented with $TiO_2$ and corona treated and is typical of polyethylene film used in disposable diaper manufacture. The bonded material is allowed to relax and age overnight. After aging, specimens 8-inches long are cut. The center 6 inch sections of the specimens are elongated to 12 inches (100% elongation) and then the polyethylene is clamped in a metal jig with the elastic surface up. The elastic is not clamped. The specimens are then placed in an oven at 100° F. for various times. The time at which a visible, continuous delamination or end release is observed is the elastic delamination resistance.

The adhesive compositions of the present invention contain at least one substantially amorphous propylene/hexene copolymer with an acid number less than about 0.5. The propylene/hexene copolymer is preferably present as an amount of 30 to about 70 weight percent of the adhesive composition, more preferably about 40 to about 65 weight percent and most preferably about 43 to about 53 weight percent. Such copolymers are known to be useful in adhesive formulations and are commercially available. The propylene/hexene copolymers can be prepared using techniques known in the art, for example, by use of the techniques disclosed in U.S. Pat. Nos. 3,954,697 and 4,259,470, both of which are incorporated herein by reference.

Preferred propylene/hexene copolymers have a melt viscosity of from about 2,000 to about 20,000 centipoise (cp) at 190° C., more preferably about 4,000 to about 20,000 cp, and most preferably about 5,300 to about 6,100 cp. Preferred copolymers are random copolymers having a 1-hexene content of about 20 to about 50 weight percent, more preferably about 30 to about 40 weight percent, and most preferably about 32 to about 36 weight percent. It is preferred that the RBSP for such copolymers is about 100° C. to about 134° C., preferably about 129° C. to about 134° C.

The low viscosity, substantially crystalline hydrocarbon wax in the adhesive composition of the present invention is present in an amount sufficient to improve the elastic delamination resistance of the composition. Typically this amount is about 1 to about 10 weight percent of the composition, preferably about 3 to about 7 weight percent. The hydrocarbon waxes in the adhesive compositions of the present invention are widely available articles of commerce and can be prepared by known techniques. These waxes are preferably polyethylene waxes. Such polyethylene waxes can be made by direct synthesis or by degrading polyethylene, preferably high density polyethylene (i.e., $\geq$ about 0.94 grams (g)/cubic centimeters (cc)) to the desired viscosity. The waxes have a melt viscosity of from about 3 to about 4,000 centipoise at 150° C., preferably about 3 to about 1,000 centipoise, and most preferably about 300 to about 700 centipoise; and a melting point of from about 90° to about 125° C., preferably about 105° C. to about 125° C., and most preferably about 120° C. to about 125° C. The waxes also preferably have a cone penetration hardness at 23° C. of about 0.1 dmm to about 10 dmm. Penetration hardness can be measured by ASTM procedure D-1321-76. Specific waxes useful in the present invention include Epolene C-15 and Epolene N-45, available from Eastman Chemical Products, Inc., Bareco 1000 and Bareco $BE^2$ 195, available from Petrolite Corp., and Paraflint H1, available from Moore and Munger, Inc. Preferred are Bareco 1000 Epolene N-45.

The adhesive compositions of the present invention typically contain one or more tackifiers in an amount of about 20 to about 60 weight percent of the composition. Solid tackifiers are typically present in an amount of from 20 to 50 weight percent, preferably 25 to 40 weight percent, and most preferably about 24 to about 29 weight percent. The solid tackifiers can be hydrocarbon resins such as DAC-B hydrocarbon resin prepared according to the process disclosed in U.S. Pat. No. 3,701,760 as well as other hydrocarbon resins, polyterpenes, and the like. One such hydrocarbon tackifying resin is a hydrocarbon resin having a softening point of about 130° C. and available commercially as Eastotac H-130 from Eastman Chemical Products, Inc. Other hydrocarbon tackifying resins can be prepared by the polymerization of monomers consisting primarily of olefins and diolefins and include, for example, the residual by-products monomers resulting from the manufacture of isoprene. These hydrocarbon tackifying resins typically exhibit a RBSP of from about 70° C. to about 145° C., preferably about 125° C. to about 135° C.; an acid number of from about 0–2, a saponification value of less than about 1; and an iodine value of from about 30 to 100. It is also preferred that such tackifiers have a melt viscosity at 190° C. of about 600 to about 1,600 cp. Examples of such commercially available resins based on a $C_5$-olefin fraction of this type are "Wingtack" 95 and "Wingtack" 115 tackifying resins sold by Goodyear Tire and Rubber Company, the Sta-Tac and Betaprene A or H resins sold by Reichold Chemical Corporation, and Escorez resins sold by Exxon Chemical Co.

Also, other suitable solid tackifier resins are the terpene polymers such as the polymeric, resinous materials obtained by polymerization and/or copolymerization of terpene hydrocarbons such as the alicyclic, monocyclic, and bicyclic monoterpenes and their mixtures, including alloocimene, carene, isomerized pinene, pinene, dipentene, terpinene, terpinolene, limonene, terpentine, a terpene cut or fraction, and various other terpenes. Particularly useful starting materials are terpene mixtures containing at least 20 percent beta-pinene and/or limonene or dipentene (racemic limonene), and the "sulfate terpentine" obtained as a by-product in the sulfate pulping process. Commercially available resins of the terpene type include the Zonarez terpene B-series and 7000 Series resins from Arizona Chemical Corp. and Nirez resins from Reichhold Chemical Corp. The typical properties reported for the Zonarez terpene resins include RBSPs of about 55° to 125° C. (ASTM E-28-67), color of 2 to 3 (Gardner 1963, 50% in heptane), acid number of less than 1 (ASTM D465-59), saponification number of less than 1 (ASTM D464-59) and specific gravity at 25° C. of about 0.96 to about 1.00 (ASTM D1963-61).

The liquid tackifiers are typically present in an amount of from 0 to about 30 weight percent of the adhesive composition, preferably about 15 to about 25 weight percent, and most preferably about 18 to about 22 weight percent. The liquid tackifiers are commercial items and/or can be prepared by techniques known in the art, for example, by the techniques described in U.S. Pat. No. 3,872,064 incorporated herein by reference. The liquid tackifiers are preferably liquid hydrocarbon resins such as synthetic polyterpene or other petroleum hydrocarbon resins. Specific examples include "Wingtrack" 10 from Goodyear Tire and Rubber Company and "Escorez" 2520 (also known as ECR-140) from Exxon Chemical Co. The liquid tackifiers have a melt viscosity of about 10,000 to about 50,000 cp at 23° C., preferably about 20,000 to about 40,000; a RBSP of about 5° C. to about 30° C., preferably about 10° C. to about 20° C., and a glass transition temperature (Tg) as measured by differential scanning calorimetry (DSC) of about $-10°$ C. to about $-30°$ C., preferably about $-20°$ C. to about $-30°$ C. A liquid tackifier is particularly useful in compositions containing a solid tackifier and substantially no plasticizing oil.

The compositions of the present invention can also optionally contain 0 to 30 weight percent of at least one plasticizing oil, preferred is about 1 to about 25 weight percent, and most preferred is about 5 to 20 weight percent. A plasticizing oil is particularly useful in compositions containing a solid tackifier and substantially no liquid tackifier. A description of suitable plasticizing oils can be found in U.S. Pat. No. 4,210,570, incorporated herein by reference. Operable plasticizing oils include paraffinic/naphthenic oils such as Shellflex 371, Tuflo 6204 and Kaydol oils, Abietol (Hercules trade name for wood rosin derivative), and polymerized DAC-B oil such as Plasticizer H. Also operable are esters derived from either aromatic or aliphatic acids within have a boiling point of greater than about 275° C. at 760 mm pressure. Useful esters include materials such as tris(2-ethylhexyl)trimellitate, bis(2-ethylhexyl)phthalate, bis(2-ethylhexyl)terephthalate, dibutyl sebacate, bis(2-ethylhexyl)adipate, 2,2,4-trimethyl-1,3-phentanediol diisobutyrate, methyl abietate, and the like. Suitable plasticizing oils have a Tg as measured by DSC of $-60°$ C. or less. Preferred plasticizing oils have a viscosity of about 325–425 Saybolt Universal Seconds (SUS) at 100° F. (37.8° C.) and a specific gravity of about 0.85–0.92 g/cc at 25° F. A specific, preferred plasticizing oil is Witco 380 from Witco Chemical Company, Sonneborn Division, Houston, Tx., U.S.A.

The adhesion compositions of this invention are prepared by blending together the adhesive components in the melt at a temperature of about 160° C. to about 200° C. until a homogeneous mixture is obtained. Various methods of blending materials of this type are known to the art and any method that produces a homogeneous mixture is satisfactory. These components blend easily in the melt and a heated vessel equipped with a stirrer is all that is required. For example, a Cowles stirrer provides effective mixing for preparing these compositions. Solvents such as hexane, heptane, mineral spirits, xylene, toluene, benzene, chlorinated hydrocarbons, etc., are not needed to prepare the compositions of this invention; however, they can be used if desired.

In addition to the hereinabove described adhesive components, it is desirable for the adhesive compositions to contain about 0.1 percent to about 1.5 percent by weight, preferably about 0.25 percent to 1.0 percent by weight, and most preferably about 0.3 to about 0.6 percent by weight, of one or more antioxidants. Antioxidants that are effective include, for example, tris(di-t-butyl-p-hydroxybenzyl)-trimethylbenze (Ionox 330), alkylated bisphenol (Naugawhite), zinc dibutyl dithiocarbamate (Butyl Zimate), and 4,4'-methylene bis(2,6-di-tert-butylphenol) (Ethyl 702), tetrakis[methylene(3,5-di-tert-butyl-4-hydroxyhydrocinnamate)methane] (Irganox 1010), Lauryl stearyl thiodipropionate (Cyanox 1212), and dilauryl 3,3'-thiodipropionate (Cyanox LTDP) and 2,6-di-tert-butyl-p-cresol (BHT) and the like.

Additional additives such as nucleating agents, pigments, colorants, fillers, solvents, and the like can also be added to the adhesive compositions of the present invention.

The adhesive compositions of the present invention can be made into any physical form typically used in the art. When formed into slats, the compositions typically are coated with a wax which may or may not be a wax within the scope of the invention.

In the method of the present invention, the adhesive composition is applied to a disposable diaper or portion thereof using techniques known in the art. For example, the adhesive composition can be applied by multiple fine line, hot-melt spray, hot-melt foam, slot coating operations, and various screen coating methods. The amount of adhesive composition applied to a diaper is that amount sufficient to result in bonds that will withstand typical storage and end use conditions. It is contemplated that the adhesive compositions of the present invention are useful in applications other than diapers, for example, in sanitary napkins and bed pad construction.

In the adhesive compositions of the present invention, as appreciated by one skilled in the art, the particular proportions of components necessary to achieve specific desired properties will vary depending on the nature of the particular components.

This invention can be further illustrated by the following examples thereof, although it will be understood that these examples are included merely for purposes of illustration and are not intended to limit the scope of the invention.

EXAMPLES 1-2

An adhesive composition was made in accordance with the present invention containing 5 weight % of a hydrocarbon wax as described herein (Example 2). For comparison, an adhesive composition outside the scope of the invention, i.e., not containing a hydrocarbon wax, was also prepared (Example 1). The two compositions were tested for their respective elastic delamination resistance (EDL). As shown in Table 1, the EDL of Example 1 was only four hours, whereas the EDL of Example 2 was greater than 100 hours.

TABLE 1

| ADHESIVE BLENDS | | |
|---|---|---|
| | EXAMPLE NUMBER | |
| | 1 | 2 |
| COMPOSITION (Weight %) | | |
| [1]APH 5 | 26 | 26 |
| [2]APH 3 | 17 | 22 |
| [3]Eastotac H-130W | 36.5 | 26.5 |
| [4]Escorez 2520 | 20 | 20 |
| [5]Bareco 1000 | — | 5.0 |
| [6]Irganox 1010 | 0.5 | 0.5 |
| BLEND PROPERTIES | | |
| VISCOSITY @ 135° C., cp | 9600 | 6600 |
| RBSP, °C. | 113 | 108 |
| CONE PENETRATION, dmm | 18 | 14 |
| TENSILE STRENGTH, psi | 15 | 30 |
| ELASTIC DELAMINATION RESISTANCE Time to failure, hrs | 4 | >100 |
| BOND STRENGTH, grams | 200 | 300 (substrate failed) |

[1]APH 5 = amorphous propylene/1-hexene copolymer having a viscosity of 17,000 cp at 190° C., 23 weight % 1-hexene content, and a RBSP of 138° C.
[2]APH 3 = amorphous propylene/1-hexene copolymer having a viscosity of 3,000 cp at 190° C., 55 weight % 1-hexene content, and a RBSP of 114° C.
[3]Eastotac H-130W = solid tackifier, petroleum hydrocarbon resin, RBSP of 130° C. melt viscosity at 190° C. of 1,000 cp.
[4]Escorez 2520 = liquid tackifier, RBSP of 20° C., Tg of −20° C., melt viscosity of 40,000 cp at 23° C.
[5]Bareco 1000 = high density, low viscosity, crystalline polyethylene wax, melting point of 113° C., penetration hardness of 1 dmm, density of 0.96 g/cc, melt viscosity of 11 cp at 150° C.
[6]Irganox 1010 = antioxidant

EXAMPLE 3-8

Adhesive blends having a relatively high proportion of propylene/1-hexane copolymer (i.e. 47%) were prepared in accordance with the present invention. The RBSPs of the blends were varied primarily by adjusting the % hexene content of the copolymer. Variations in the elastic delamination resistance (EDL) were observed, however, in all cases the EDLs were greater than four hours as shown in Table 2.

TABLE 2

| ADHESIVE BLENDS | | | | | | |
|---|---|---|---|---|---|---|
| | EXAMPLE NUMBER | | | | | |
| | 3 | 4 | 5 | 6 | 7 | 8 |
| BLEND COMPOSITION (Wt %) | | | | | | |
| [1]APH | 47.0 | 47.0 | 47.0 | 47.0 | 47.0 | 47.0 |
| [2]Escorez 2520 | 19.5 | 19.5 | 19.5 | 19.5 | 19.5 | 19.5 |
| [3]Eastotac H-130W | 26.0 | 26.0 | 26.0 | 26.0 | 26.0 | 26.0 |
| [4]Bareco 1000 | 3.0 | 3.0 | 3.0 | 3.0 | 3.0 | 3.0 |
| [5]Epolene C-15 | 4.0 | 4.0 | 4.0 | 4.0 | 4.0 | 4.0 |
| [6]Irganox 1010 | 0.5 | 0.5 | 0.5 | 0.5 | 0.5 | 0.5 |
| PHYSICAL PROPERTIES OF APH | | | | | | |
| Viscosity @ 375° F., cp | 5475 | 8325 | 7650 | 9550 | 7000 | 5300 |
| RBSP, °C. | 132 | 138 | 135 | 132 | 124 | 126 |
| Wt. % Hexene | 36 | 33 | 35 | 36 | 40 | 40 |
| PHYSICAL PROPERTIES OF BLEND | | | | | | |
| Viscosity @ 135° C., cp | 8500 | 22750 | 29000 | 19000 | 7750 | 6440 |
| RBSP, °C. | 111 | 120.5 | 116.5 | 112 | 107 | 107 |
| Cone Penetration, dmm | 25 | 23.5 | 24 | 22 | 23 | 26 |
| ELASTIC DELAMINATION RESISTANCE Time to failure, hrs | >47 | >47 | >4 | >4 | >4 | >8 |

[1]APH = amorphous propylene/1-hexane copolymer
[2]Escorez 2520 = liquid tackifier, RBSP of 20° C., Tg of −20° C., melt viscosity at 23° C. of 40,000 cp.
[3]Eastotac H-130W = solid tackifier, petroleum hydrocarbon resin, RBSP of 130° C., melt viscosity at 190° C. of 1,000 cp.
[4]Bareco 1000 = high density, low viscosity, crystalline polyethylene wax, melting point of 113° C., penetration hardness of 1 dmm, density of 0.96 g/cc, melt viscosity of 11 cp at 150° C.
[5]Epolene C-15 = lower density, low viscosity, crystalline polyethylene wax, melting point of 102° C., penetration hardness of 4 dmm, density of 0.91 g/cc, melt viscosity of 3,900 cp at 150° C.
[6]Irganox 1010 = antioxidant

EXAMPLES 9-16

Adhesive blends were prepared in accordance with the present invention. The compositions and properties of these blends are shown in Table 3. Example 14 is a comparative example without a wax.

TABLE 3

ADHESIVE BLENDS

| | EXAMPLE NUMBER | | | | | | | |
|---|---|---|---|---|---|---|---|---|
| | 9 | 10 | 11 | 12 | 13 | 14 | 15 | 16 |
| COMPOSITION (Wt. %) | | | | | | | | |
| [1]APH | 48 | — | 48 | 48 | 48 | 50.5 | 50 | 45.7 |
| [2]APB | — | 54.5 | — | — | — | — | — | — |
| [3]Eastotac H-130W | 26.5 | 20 | 26.5 | 26.5 | 26.5 | 27.9 | 17.6 | 25.2 |
| [4]Escorez 2520 | 20 | 20 | 20 | 20 | 20 | 21.1 | 20.8 | 19 |
| [5]Bareco 1000 | 5 | — | — | — | — | — | — | — |
| [6]Epolene N-45 | — | 5 | — | — | — | — | 1 | 10 |
| [7]Epolene C-15 | — | — | 5 | — | — | — | — | — |
| [8]Bareco Be[2] 195 | — | — | — | 5 | — | — | — | — |
| [9]Paraflint H-1 | — | — | — | — | 5 | — | — | — |
| [10]Irganox 1010 | 0.5 | 0.5 | 0.5 | 0.5 | 0.5 | 0.5 | 0.5 | 0.5 |
| PHYSICAL PROPERTIES OF APH AND APB | | | | | | | | |
| Viscosity @ 375° F. (190° C.), cp | 5475 | 10000 | 5475 | 5475 | 5475 | 5475 | 5475 | 5475 |
| RBSP, °C. | 132 | 110 | 132 | 132 | 132 | 132 | 132 | 132 |
| Wt. % Hexene | 36 | 0 | 36 | 36 | 36 | 36 | 36 | 36 |
| Wt. % Butene | 0 | 40 | 0 | 0 | 0 | 0 | 0 | 0 |
| PHYSICAL PROPERTIES OF WAX | | | | | | | | |
| Melting point, °C. | 113 | 123 | 102 | 91 | 13 | — | 123 | 123 |
| Density, g/cc | 0.96 | 0.95 | 0.91 | 0.93 | 0.94 | — | 0.95 | 0.95 |
| Viscosity @ 150° C., cp | 11 | 500 | 3900 | 3 | 3 | — | 500 | 500 |
| Wax type | ethylene | ethylene | ethylene | microcrystalline | Fischer-Tropsch | — | ethylene | ethylene |
| Penetration Hardness, dmm | 0.5 | 0.1 | 4 | 7 | 2 | — | 0.1 | 0.1 |
| BLEND PROPERTIES | | | | | | | | |
| VISCOSITY @ 135° C., cp | 8000 | 10500 | 8000 | 4880 | 4880 | 6880 | 7100 | 4200 |
| RBSP, °C. | 117 | 117 | 117 | 111 | 103 | 113 | 115 | 117 |
| CONE PENETRATION, dmm | 17 | 18 | 39 | 10 | 18 | 42 | 33 | 14 |
| ELASTIC DELAMINATION RESISTANCE Time to failure, hrs | 24 | 24 | 24 | 24 | 24 | <1 | 24 | >72 |

[1]APH = amorphous propylene/1-hexene copolymer
[2]APB = amorphous propylene/1-butene copolymer
[3]Eastotac H-130W = solid tackifier
[4]Escorez 2520 = liquid tackifier
[5]Bareco 1000 = wax
[6]Epolene N-45 = wax
[7]Epolene C-15 = wax
[8]Bareco Be[2] 195 = wax
[9]Paraflint H-1 = wax
[10]Irganox 1010 = antioxidant

EXAMPLES 17-25

Adhesive blends were prepared in accordance with the present invention. The compositions and properties of these blends are shown in Table 4. Example 17 is a typical example of the invention. Examples 18 and 19 are comparative examples using a paraffin wax outside the scope of the present invention which does not provide the required elastic delamination resistance. Example 20 is a control comparative example with no wax which does not have the required elastic delamination resistance. Example 21 is an example of the present invention illustrating the use of only one tackifier. Examples 22-25 are examples of the present invention which illustrate the use of a plasticizing oil.

TABLE 4

ADHESIVE BLENDS

| | EXAMPLE NUMBER | | | | | | | | |
|---|---|---|---|---|---|---|---|---|---|
| | 17 | 18 | 19 | 20 | 21 | 22 | 23 | 24 | 25 |
| BLEND COMPOSITION (Wt. %) | | | | | | | | | |
| [1]APH 1 | 48 | 48 | 43 | 50.5 | 48 | — | — | — | — |
| [2]APH 2 | — | — | — | — | — | 50 | 50 | 50 | 50 |
| [3]Escorez 2520 | 20 | 20 | 20 | 21.1 | — | — | — | — | — |
| [4]Eastotac H-130 W | 26.5 | 26.5 | 26.5 | 27.9 | — | 38.5 | 35.5 | 32.5 | 29.5 |
| [5]Nirez M-85 | — | — | — | — | 46.5 | — | — | — | — |
| [6]Epolene N-45 | 5 | — | — | — | — | 4 | 4 | 4 | 4 |
| [7]Moore & Munger R-0845 | — | 5 | 10 | — | — | — | — | — | — |
| [8]Witco 380 | — | — | — | — | — | 7 | 10 | 13 | 16 |
| [9]Bareco 1000 | — | — | — | — | 5 | — | — | — | — |
| [10]Irganox 1010 | 0.5 | 0.5 | 0.5 | 0.5 | 0.5 | 0.5 | 0.5 | 0.5 | 0.5 |
| BLEND PROPERTIES | | | | | | | | | |
| Viscosity | | | | | | | | | |

TABLE 4-continued

| | ADHESIVE BLENDS | | | | | | | | |
|---|---|---|---|---|---|---|---|---|---|
| | EXAMPLE NUMBER | | | | | | | | |
| | 17 | 18 | 19 | 20 | 21 | 22 | 23 | 24 | 25 |
| @ 225° F., cp | 500000 | 197500 | 360000 | 70250 | 47500 | | | | |
| @ 275° F., cp | 7940 | 6000 | 2450 | 6875 | 7560 | 11800 | 9400 | 7440 | 6265 |
| @ 325° F., cp | 2475 | 2315 | 890 | 1990 | 2400 | | | | |
| RBSP, °C. | 112 | 106.5 | 110 | 113 | 107 | 115.5 | 116 | 115.5 | 115 |
| Cone Penetration, dmm | 20 | 36 | 21.5 | 42.5 | 11 | 10.5 | 13.5 | 19.5 | 24 |
| ELASTIC DELAMINATION RESISTANCE Time to Failure, hrs | >8 | ≦1 | ≦1 | ≦1 | >8 | >8 | >8 | >8 | >8 |

[1]APH 1 = amorphous propylene/hexene copolymer having 38 wt. % hexene (melt viscosity of 6000 cps at 190° C., 126° C. RBSP)
[2]APH 2 = amorphous propylene/hexene copolymer having 37 wt. % hexene (melt viscosity of 5500 cps at 190° C., 128° C. RBSP)
[3]Escorez 2520 = liquid tackifier (see Table 2 for properties)
[4]Eastotac H-130W = solid tackifier (see Table 2 for properties)
[5]Nirez M-85 = solid tackifier which is an aromatic modified polyterpene resin made by Reichhold Chemicals, Inc., White Plains, New York; RBSP of 82-88° C., specific gravity of 0.995
[6]Epolene N-45 = wax (see Table 3 for properties)
[7]Moore and Munger R-0845 = paraffin wax (melt viscosity of 43 cp at 210° F. (99° C.), 145° F. (63° C.) melting point, 16 dmm cone penetration), available from Moore and Munger Marketing, Inc., 140 Sherman Street, Fairfield, Connecticut 06430
[8]Witco 380 = plasticizing oil, viscosity of 375 SUS at 100° F. (37.8° C.), specific gravity at 25° F. of 0.8664
[9]Bareco 1000 = wax (see Table 3 for properties)
[10]Irganox 1010 = antioxidant

EXAMPLES 26-28

Adhesive blends were prepared in accordance with the present invention. The compositions and properties of these blends are shown in Table 5. Example 26 is a control comparative example without a wax. Example 27 is a typical example of the present invention with 5% wax. Example 28 is a comparative example wherein a wax outside the scope of the invention was used which does not provide the required elastic delamination resistance.

TABLE 5

| | ADHESIVE BLENDS | | |
|---|---|---|---|
| | EXAMPLE NUMBER | | |
| | 26 | 27 | 28 |
| BLEND COMPOSITION (Wt %) | | | |
| [1]APH | 50.5 | 48.0 | 48.0 |
| [2]Escorez 2520 | 21.1 | 20.0 | 20.0 |
| [3]H130W | 27.9 | 26.5 | 26.5 |
| [4]N45 | — | 5.0 | — |
| [5]Moore & Munger R-4044 | — | — | 5.0 |
| [6]Irganox 1010 | 0.5 | 0.5 | 0.5 |
| PHYSICAL PROPERTIES | | | |
| Viscosity @ 275° F. | 8538 | 7400 | 5350 |
| RBSP, °C. | 112.8 | 116.8 | 110.5 |
| Cone Penetration, dmm | 30.5 | 14.0 | 27.0 |
| ELASTIC DELAMINATION RESISTANCE Time to failure, hrs | ≦4 | >24 | ≦4 |

[1]APH = amorphous propylene/hexene copolymer having 34 wt % hexene, RBSP of 131.5° C., melt viscosity of 5700 cp at 190° C.
[2]Escorez 2520 = liquid tackifier (see Table 2 for properties)
[3]Eastotac H-130W = solid tackifier (see Table 2 for properties)
[4]N45 = wax (Epolene N-45, see Table 3 for properties)
[5]Moore & Munger R-4044 = paraffin wax, viscosity of 41 cp at 210° F. (99° C.), melting point of 142° F. (61° C.), cone penetration hardness of 13 dmm, density of 0.79 g/cc
[6]Irganox 1010 = antioxidant

We claim:

1. A method comprising applying an adhesive composition to a disposable diaper or portion thereof, wherein said adhesive composition is a hot-melt adhesive composition having a melt viscosity of about 3,000 to about 25,000 centipoise at 135° C., a cone penetration value as measured by ASTM Procedure D-1403 of at least 10 dmm, and a Ring and Ball softening point of about 90° C., to about 125° C., said composition a blend of:

(a) at least one substantially amorphous propylene/hexene copolymer having an acid number of less than about 0.5,
   (b) at least one tackifier, and
   (c) at least one substantially crystalline, low viscosity hydrocarbon wax containing substantially no propylene and having a melt viscosity of from about 3 to about 4,000 centipoise at 150° C. and a melting point of from about 90° C. to about 125° C., the concentrations of components (a), (b), and (c) being such that said adhesive composition has an elastic delamination resistance of at least about 4 hours wherein elastic delamination resistance is the length of time a polyethylene to elastic bond can withstand the stress of elastic relaxation at body temperature.

2. A method comprising applying an adhesive composition to a disposable diaper or portion thereof, wherein said adhesive composition is a hot-melt adhesive composition having a melt viscosity of about 3,000 to about 25,000 centipoise at 135° C., a cone penetration value as measured by ASTM Procedure D-1403 of at least 10 dmm, and a Ring and Ball softening point of about 90° C. to about 125° C., said composition comprising a blend of:

(i) about 30 to about 70 weight percent of at least one substantially amorphous propylene/hexene random copolymer containing from about 20 to about 50 weight percent of 1-hexene said copolymer having a melt viscosity of from about 2,000 to about 20,000 centipoise at 190° C.,
   (ii) about 20 to about 50 weight percent of at least one solid tackifier comprising hydrocarbon resins or polyterpene resins said tackifier having a softening point of from about 70° C. to about 145° C.
   (iii) 0 to about 30 weight percent of at least one liquid tackifier having a viscosity of from about 10,000 to about 50,000 centipoise at 23° C. and a Ring and Ball softening point of from about 5° C. to about 30° C.,
   (iv) from about 1 to about 10 weight percent of at least one high density, substantially crystalline, low viscosity hydrocarbon wax containing substantially no propylene and having a melt viscosity of from about 3 to about 4,000 centipoise at 150° C. and melting point of from about 90° C. to about 125° C., and (v) 0 to about 30 weight percent of at least one plasticizing oil.

3. A method comprising applying an adhesive composition to a disposable diaper or portion thereof, wherein said adhesive composition is a hot-melt adhesive composition having a melt viscosity of about 5,000 to about 9,000 at 135° C., a cone penetration value as measured by ASTM Procedure D-1403 of at least 10 dmm, a Ring and Ball softening point of about 112° C. to about 125° C., and a Gardner color of less than about 7, said composition comprising a blend of:
- (a) about 43 to about 53 weight percent of at least one substantially amorphous propylene/hexene random copolymer containing from about 32 to about 36 weight percent of 1-hexene, said copolymer having a melt viscosity of from about 5,300 to about 6,100 centipoise at 190° C. and a Ring and Ball softening point of about 129° C. to about 134° C.,
- (b) about 24 to about 29 weight percent of at least one solid tackifier comprising a hydrocarbon resin, said solid tackifier having a Ring and Ball softening point of about 125° C. to about 135° C. and melt viscosity at 190° C. of about 600 to about 1,600 centipoise,
- (c) about 18 to about 22 weight percent of at least one liquid tackifier comprising a hydrocarbon resin, said liquid tackifier having a Ring and Ball softening point of about 10° C. to about 20° C., a melt viscosity of about 20,000 to about 40,000 centipoise at 23° C. and a Tg as measured by DSC of about −10° C. to about −30° C.,
- (d) about 3 to about 7 weight percent of at least one high density, substantially crystalline, low viscosity polyethylene wax containing substantially no propylene and having a melt viscosity of from about 300 to about 700 centipoise at 150° C. and a melting point of about 120 to about 125° C., and
- (e) about 0.3 to about 0.6 weight percent of at least one antioxidant.

4. An article comprising a disposable diaper having applied thereon a hot-melt adhesive composition having a melt viscosity of about 3,000 to about 25,000 centipoise at 135° C., a cone penetration value as measured by ASTM Procedure D-1403 of at least 10 dmm, and a Ring and Ball softening point of about 90° C. to about 125° C., said composition comprising a blend of:
- (a) at least one substantially amorphous propylene/hexene copolymer having an acid number of less than about 0.5,
- (b) at least one tackifier, and
- (c) at least one substantially crystalline, low viscosity hydrocarbon wax containing substantially no propylene and having a melt viscosity of from about 3 to about 4,000 centipoise at 150° C. and a melting point of from about 90° C. to about 125° C., the concentrations of components (a), (b), and (c) being such that said adhesive composition has an elastic delamination resistance of at least about 4 hours wherein elastic delamination resistance is the length of time a polyethylene to elastic bond can withstand the stress of elastic relaxation at body temperature.

5. An article comprising a disposable diaper having applied thereon a hot-melt adhesive composition having a melt viscosity of about 3,000 to about 25,000 centipoise at 135° C., a cone penetration value as measured by ASTM Procedure D-1403 of at least 10 dmm, and a Ring and Ball softening point of about 90° C. to about 125° C., said composition comprising a blend of:
- (i) about 30 to about 70 weight percent of a least one substantially amorphous propylene/hexene random copolymer containing from about 20 to about 50 weight percent of 1-hexene said copolymer having a melt viscosity of from about 2,000 to about 20,000 centipoise at 190° C.,
- (ii) about 20 to about 50 weight percent of at least one solid tackifier comprising hydrocarbon resins or polyterpene resins said tackifier having a softening point of from about 70° C. to about 145° C.
- (iii) 0 to about 30 weight percent of at least one liquid tackifier having a viscosity of from about 10,000 to about 50,000 centipoise at 23° C. and a Ring and Ball softening point of from about 5° C. to about 30° C.,
- (iv) from about 1 to about 10 weight percent of at least one high density, substantially crystalline, low viscosity hydrocarbon wax containing substantially no propylene and having a melt viscosity of from about 3 to about 4,000 centipoise at 150° C. and a melting point of from about 90° C. to about 125° C., and
- (v) 0 about 30 weight percent of at least one plasticizing oil.

6. An article comprising a disposable diaper having applied thereon a hot-melt adhesive composition having a melt viscosity of about 5,000 to about 9,000 at 135° C., a cone penetration value as measured by ASTM Procedure D-1403 of at least 10 dmm, a Ring and Ball softening point of about 112° C. to about 125° C., and a Gardner color of less than about 7, said composition comprising a blend of:
- (a) about 43 to about 53 weight percent of at least one substantially amorphous propylene/hexene random copolymer containing from about 32 to about 36 weight percent of 1-hexene, said copolymer having a melt viscosity of from about 5,300 to about 6,100 centipoise at 190° C. and a Ring and Ball softening point of about 129° C. to about 134° C., about 24 to about 29 weight percent of at least one solid tackifier comprising a hydrocarbon resin, said solid tackifier having a Ring and Ball softening point of about 125° C. to about 135° C. and a melt viscosity at 190° C. of about 600 to about 1,600 centipoise,
- (c) about 18 to about 22 weight percent of at least one liquid tackifier comprising a hydrocarbon resin, said liquid tackifier having a Ring and Ball softening point of about 10° C. to about 20° C., a melt viscosity of about 20,000 to about 40, 000 centipoise at 23° C. and a Tg as measured by DSC of about −10° C. to about −30° C.,
- (d) about 3 to about 7 weight percent of at least one high density, substantially crystalline, low viscosity polyethylene wax containing substantially no propylene and having a melt viscosity of from about 300 to about 700 centipoise at 150° C. and a melting point of about 120 to about 125° C., and
- (e) about 0.3 to about 0.6 weight percent of at lesat one antioxidant.

* * * * *